United States Patent [19]
Ootsu et al.

[11] 4,400,295
[45] Aug. 23, 1983

[54] EMULSIFIER COMPOSITION

[75] Inventors: Yoshiro Ootsu, Minoo; Yaeno Arima, Kobe, both of Japan

[73] Assignee: Loire Cosmetics Co., Ltd., Tokyo, Japan

[21] Appl. No.: 130,858

[22] Filed: Mar. 17, 1980

[30] Foreign Application Priority Data

Mar. 24, 1979 [JP] Japan ................... 54-34961
Mar. 24, 1979 [JP] Japan ................... 54-34962
Mar. 24, 1979 [JP] Japan ................... 54-34963
Mar. 24, 1979 [JP] Japan ................... 54-34964
May 29, 1979 [JP] Japan ................... 54-66671

[51] Int. Cl.³ ............ B01F 17/28; B01F 17/34; B01F 17/38; B01F 17/42
[52] U.S. Cl. ............... 252/356; 252/309; 252/312; 252/314; 252/DIG. 1; 252/DIG. 5; 424/63; 424/172
[58] Field of Search ........... 252/356, 357, DIG. 1, 252/DIG. 5; 424/172

[56] References Cited

U.S. PATENT DOCUMENTS

| Re. 21,322 | 1/1940 | Harris | 252/356 X |
| 2,047,069 | 7/1936 | Hentrich et al. | 252/356 X |
| 2,090,537 | 8/1937 | Lund | 252/356 X |
| 2,870,201 | 1/1959 | Pollack | 562/562 |
| 4,206,070 | 6/1980 | Jones | 252/DIG. 1 |
| 4,218,334 | 8/1980 | Lundmark | 252/356 |

OTHER PUBLICATIONS

*Cosmetics: Science and Technology*, Edited by Balsam et al., 2nd Edition, vol. 3, John Wiley & Sons, (1974), pp. 581-611.

Primary Examiner—Richard D. Lovering
Attorney, Agent, or Firm—Darby & Darby

[57] ABSTRACT

Emulsifier composition which comprises a condensation product of a fatty acid and a basic amino acid, and at least one secondary compound selected from the group consisting of a sterol compound, a fatty acid ester of polyhydric alcohol, a diol compound having hydroxyl groups at α and β positions, a glycerophosphoric acid ester and a higher alcohol. Various creams and lotions can readily be prepared using the emulsifier composition.

13 Claims, No Drawings

EMULSIFIER COMPOSITION

BACKGROUND OF THE INVENTION

The present invention relates to an emulsifier composition by which various creams and lotions can be readily prepared. More particularly, the present invention relates to an emulsifier composition which comprises a condensation product of a fatty acid and a basic amino acid, and a secondary compound selected from the group consisting of a sterol compound, a fatty acid ester of polyhydric alcohol, a diol compound having hydroxyl groups at $\alpha$ and $\beta$ positions, a glycerophosphoric acid ester and a higher alcohol.

Heretofore, the emulsion has been prepared using selectively a lipophilic emulsifier and/or a hydrophilic emulsifier. That is to say, the emulsion has been prepared using at least two emulsifiers selected from the group consisting of an anionic surface active agent, a cationic surface active agent and a nonionic surface active agent in view of a predetermined hydrophilic-lipophilic balance (hereinafter referred to as HLB) of oily material of the emulsion. Particularly, anionic surface active agents such as fatty acid soaps and ether type, ester type or amide type nonionic surface active agents are used widely in combination. However, such emulsifier composition has been found unsatisfactory in that it fails to meet all of the following requirements. (1) The emulsifier is not irritating to the skin, and action against the skin is mild. (2) The emulsion should be stable, and deterioration of products such as creams and lotions does not occur. (3) Usability and appearance of the products are excellent. Further, the emulsifier composition of cholesterol and/or cetyl alcohol and sulfuric acid ester of aliphatic higher alcohols such as cetyl alcohol has been proposed. When such emulsifier composition is used, interfacial complex compounds can be formed at interfaces between water and oily material, and therefore a stable emulsion can be prepared. However, the sulfuric acid ester of aliphatic higher alcohol irritates the skin, and therefore it is not preferable to use it.

SUMMARY OF THE INVENTION

It is, therefore, an object of the present invention to provide a novel emulsifier composition which does not irritate the skin.

It is a further object of the present invention to provide a novel emulsifier composition by which various creams and lotions having a good stability can be readily prepared.

It is a still further object of the present invention to provide a novel emulsifier composition by which there can be prepared various creams and lotions having an excellent usability and appearance.

Other objects and advantages of the present invention will become readily apparent to those skilled in the art from the following description.

These objects are achieved by the present invention which is directed to an emulsifier composition which comprises a condensation product of a fatty acid and a basic amino acid, and at least one secondary compound selected from the group consisting of a sterol compound, a fatty acid ester of polyhydric alcohol, a diol compound having hydroxyl groups at $\alpha$ and $\beta$ positions, a glycerophosphoric acid ester and a higher alcohol.

DETAILED DESCRIPTION OF THE INVENTION

One component used in the present invention is a condensation product of a fatty acid and a basic amino acid. The condensation product may be used along or in combination in the present invention. The condensation product is obtained by reacting a fatty acid with a basic amino acid. The fatty acids used for production of the condensation product include straight chain saturated fatty acids having 8 to 40 carbon atoms, branched chain saturated fatty acids having 8 to 40 carbon atoms, straight chain unsaturated fatty acids having 8 to 40 carbon atoms, and branched chain unsaturated fatty acids having 8 to 40 carbon atoms. Representative fatty acids include lauric acid, myristic acid, palmitic acid, stearic acid, behenic acid, oleic acid, undecylenic acid, linoleic acid, linolenic acid, hydroxystearic acid, cerotic acid, abietic acid, ricinoleic acid, isostearic acid, 2-ethylhexadecanoic acid, 2-heptylundecanoic acid, 2-octyldecanoic acid, lanolin fatty acid, 12-methyl-9, 11-octadecadienoic acid and the like. The basic amino acids used for the production of the condensation product include arginine, lysine, hydroxylysine $\beta$-lysine, histidine, ornithine, canavanine citrulline thiolhistidine and hydroxylysine and the like. D form, L form and mixture thereof may be used as the basic amino acid in the present invention.

The other component used in the present invention is a secondary compound selected from the group consisting of a sterol compound, a fatty acid ester of polyhydric alcohol, a diol compound having hydroxyl groups at $\alpha$ and $\beta$ positions, a glycerophosphoric acid ester and a higher alcohol.

The sterol compounds usable for the present invention include cholesterol, cholestanol, phytosterols (sitosterol, stigmasterol, campesterol) phytostanol which is obtained by hydrogenation of phytosterol, ergosterol, brassicasterol, spinasterol, fucosterol, various sterol mixtures which are contained in unsaponifiable matter of lanolin and the like.

The fatty acid ester of polyhydric alcohol is obtained by reacting a fatty acid with a polyhydric alcohol. The fatty acid ester of polyhydric alcohol is a mixture of partially esterified materials such as monoester, diester, triester, tetraester, pentaester. The ratio of these esters varies depending upon the kind of fatty acids and the number of hydroxyl group of polyhydric alcohols. The polyhydric alcohols used for the production of the fatty acid ester of polyhydric alcohol include glycerol, polyglycerols (diglycerol, triglycerol, tetraglycerol, pentaglycerol, hexaglycerol, octaglycerol, monaglycerol, decaglycerol and the like), pentaerythritol, sorbitan, sorbitol mannitol, sucrose and the like. The fatty acids used for production of the fatty acid ester of polyhydric alcohol include straight chain saturated fatty acids, branched chain saturated fatty acids, straight chain unsaturated fatty acids and branched chain unsaturated fatty acids. Representative fatty acids usable for the present invention include caprylic acid, capric acid, lauric acid, myristic acid, palmitic acid, stearic acid, behenic acid, oleic acid, linoleic acid, linolenic acid, ricinoleic acid, isostearic acid, undecylenic acid, hydroxystearic acid, cerotic acid, abietic acid, isooctanoic acid, isohexadecanoic acid, 2-ethylhexadecanoic acid, lanolin fatty acid, 12-methyl-9, 11-octadecadienoic acid and the like.

The diol compounds having hydroxyl groups at α and β positions include (a) 1,2-long chain alkane diol having 10 to 40 carbon atoms, (b) glycerol monoalkyl ether having 8 to 40 carbon atoms, (c) mixtures thereof. Representative 1,2-long chain alkane diols include reaction products obtained by hydroxylation of α-olefinic compounds, and straight chain, iso- or antiiso 1,2-long chain alkane diols present in unsaponifiable matters of natural lanolin. Representative glycerol monoalkyl ethers include glycerol monomyristyl ether obtained by reacting glycerol monosodium with myristyl sulfate, glycerol monolauryl ether obtained by reacting glycerol monosodium with lauryl sulfate, chimyl alcohol $C_{16}H_{33}OCH_2CH(OH)\text{-}CH_2OH$, batyl alcohol $C_{18}H_{37}OCH_2CH(OH)CH_2OH$, celakyl alcohol $C_{18}H_{35}OCH_2CH(OH)CH_2OH$ and the like. These alcohols are present in unsaponifiable matters of liver oil which is obtained from animals such as a shark, a ray, a crab and a cuttle fish.

The glycerophosphoric acid ester is a compound having the following formula

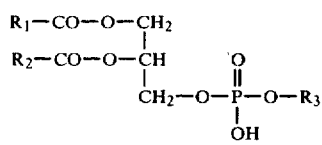

wherein $R_1$ and $R_2$ are hydrogen, saturated hydrocarbon having 8 to 40 carbon atoms or unsaturated hydrocarbon having 8 to 40 carbon atoms respectively, and $R_3$ is hydrogen, choline, ethanolamine, serine, inositol, glycerol, N-methylethanolamine or N,N-dimethylethanolamine. The glycerophosphoric acid ester may be used alone or in combination in the present invention. Representative glycerophosphoric acid esters include phosphatidic acid, phosphatidyl choline (lecithin), phosphatidyl ethanolamine, phosphatidyl serine, phosphatidyl-N-methylenethanolamine, phosphatidyl-N,N-dimethylethanolamine, phosphatidyl glycerol, phosphatidyl inositol, lysophosphatidyl choline and the like.

The higher alcohols include straight chain saturated higher alcohols having 8 to 40 carbon atoms, branched chain saturated higher alcohols having 8 to 40 carbon atoms, straight chain unsaturated higher alcohols having 8 to 40 carbon atoms and branched chain unsaturated higher alcohols having 8 to 40 carbon atoms. Representative higher alcohols usable for the present invention include lauryl alcohol, myristyl alcohol, cetyl alcohol, stearyl alcohol, behenyl alcohol, beef tallow alcohol, sperm alcohol, oleyl alcohol, cetostearyl alcohol, isostearyl alcohol, 2-octyldodecanol, 2-hexyldecanol, octyl alcohol, decyl alcohol, arachidic alcohol, coconut alcohol, lanolin alcohol, isocetyl alcohol, octadecanol glycol and the like.

The weight ratio of the condensation product to the secondary compound is 20:1 to 1:20, preferably 10:1 to 1:10.

The emulsifier composition is obtained by mixing the secondary compound with the condensation product which was beforehand prepared by reacting the fatty acid and the basic amino acid. The emulsifier composition is also obtainable by mixing fatty acid, basic amino acid and secondary compound simultaneously.

The oily materials such as animal oils and fats, vegetable oils and fats, mineral oils, waxes, synthetic esters and the like may be emulsified by the emulsifier composition of the present invention. The emulsion obtained is stable for a long time. In the meanwhile, it is possible to add well known surface active agents as optional component. Surprisingly, a sufficiently emulsified emulsion can be prepared regardless of HLB of the surface active agent.

When various additives such as preservatives, humectants, thickeners, germicides, ultraviolet absorbers, pigments, pharmaceutical agents, perfumes and the like are added in combination to the emulsion obtained by emulsifying the oily materials by means of the emulsifier composition of the present invention, various creams such as a vanishing cream, a cleansing cream, a make-up cream, oil-in-water cream, water-in-oil cream a nutrient cream, and various lotions such as a milk lotion as well as pharmaceutical products such as a hydrophilic ointment may be prepared.

As described above, the emulsifier composition of the present invention comprises a condensation product of a fatty acid and a basic amino acid, and a secondary compound selected from the group consisting of a sterol compound, a fatty acid ester of polyhydric alcohol, a diol compound having hydroxyl groups at α and β positions, a glycerophosphoric acid ester and a higher alcohol. The oily materials can be readily emulsified by means of the emulsifier composition of the present invention. As the interfacial complex can be formed by the two components, the emulsion formed by using the emulsifier composition of the present invention has an excellent stability. Further, final products such as various creams and lotions have an excellent performance. That is to say, the final products do not irritate the skin, and action against to the skin is mild. Furthermore, the final products have an excellent usability and appearance.

The following examples are given as specific illustrations of the present invention. It should be understood, however, that the present invention is not limited to the specific details set forth in the examples. All values shown in percent in the examples are by weight percent. The term "lecithin" appeared in the examples means soybean lecithin in which phosphatidyl choline, phosphatidyl ethanolamine, phosphatidyl serine, phosphatidyl inositol and the like are present in combination.

EXAMPLE 1

| | | Percent |
|---|---|---|
| (1) | Liquid paraffin | 20.0 |
| (2) | Cholesterol | 2.0 |
| (3) | Condensation product of MC stearic acid and lysine | 4.0 |
| (4) | Purified water | 74.0 |
| | | 100.0 |

Components 1 and 2 as described above were charged into a beaker, and then melted at a temperature of 80° C. to form a mixture.

Component 3 as described above was added to the purified water contained in another beaker, and then dissolved into the purified water at a temperature of 80° C. to prepare an aqueous solution.

Thereafter, the aqueous solution as prepared above was added to the mixture. The formulation was stirred for 5 minutes at a temperature of 80° C. to allow it to emulsify uniformly, and then cooled with stirring. A portion of emulsion obtained was placed into a thermohygrostat at a temperature of 40° C. so as to determine a thermal resistance of the emulsion. No break of the emulsion occurred after the lapse of 30 days. It is apparent that the emulsion obtained in Example 1 has an excellent stability.

EXAMPLES 2–6

Example 1 was repeated with the exception that isopropyl myristate, cetostearyl 2-ethylhexanoate, squalane, saturated fatty acid ($C_8$–$C_{12}$)triglyceride or castor oil was used instead of the liquid paraffin used in Example 1 as oily material. The emulsions obtained in Examples 2–6 were emulsified sufficiently like in the case of the emulsion of Example 1, and had a sufficient stability.

EXAMPLE 7

Vanishing cream

|      |                                                   | Percent |
|------|---------------------------------------------------|---------|
| (1)  | MC stearic acid                                   | 3.0     |
| (2)  | Paraffin wax (135° F.)                            | 2.0     |
| (3)  | Spermaceti                                        | 5.0     |
| (4)  | Cetyl alcohol                                     | 2.0     |
| (5)  | Cetyl isooctanate                                 | 5.0     |
| (6)  | Isopropyl myristate                               | 2.0     |
| (7)  | Cholesterol                                       | 2.0     |
| (8)  | Butyl para-hydroxybenzoate                        | 0.1     |
| (9)  | Methyl para-hydroxybenzoate                       | 0.1     |
| (10) | Condensation product of MC stearic acid and arginine | 2.0  |
| (11) | Glycerol                                          | 5.0     |
| (12) | Purified water                                    | 71.6    |
| (13) | Perfume                                           | 0.2     |
|      |                                                   | 100.0   |

Components 1–8 as described above were charged into a beaker, and then melted at a temperature of 80° C. to form a mixture.

Components 9–11 as described above were added to the purified water contained in another beaker, and then dissolved into the purified water at a temperature of 80° C. to prepare an aqueous solution.

Thereafter, the aqueous solution as prepared above was added to the mixture. The formulation was stirred for 5 minutes at a temperature of 80° C. to allow it to emulsify uniformly, and then cooled with stirring. Component 13, i.e., perfume was added to the emulsion at a temperature of 45° C. The vanishing cream obtained was a stable emulsion, and action against the skin was mild.

EXAMPLE 8

Cleansing cream

|                                                | Percent |
|------------------------------------------------|---------|
| Bees wax                                       | 3.0     |
| Paraffin wax (135° F.)                         | 2.0     |
| Cetyl alcohol                                  | 2.0     |
| Isopropyl palmitate                            | 10.0    |
| Liquid paraffin                                | 30.0    |
| Phytosterol                                    | 2.0     |
| Butyl para-hydroxybenzoate                     | 0.1     |
| Methyl para-hydroxybenzoate                    | 0.1     |
| Condensation product of MC stearic acid and L-lysine | 4.0 |
| Propylene glycol                               | 5.0     |
| Purified water                                 | 41.6    |
| Perfume                                        | 0.2     |
|                                                | 100.0   |

Each component was added and emulsified in the manner of Example 7. The cleaning cream obtained was a stable emulsion, and action against the skin was mild.

EXAMPLE 9

Milk lotion

|                                                          | Percent |
|----------------------------------------------------------|---------|
| Spermaceti                                               | 3.0     |
| Cetyl alcohol                                            | 1.0     |
| Bees wax                                                 | 2.0     |
| Saturated fatty acid ($C_8$–$C_{12}$) triglyceride       | 10.0    |
| Cholesterol                                              | 2.0     |
| Butyl para-hydroxybenzoate                               | 0.1     |
| Methyl para-hydroxybenzoate                              | 0.1     |
| Condensation product of isostearic acid and L-arginine   | 2.0     |
| Glycerol                                                 | 5.0     |
| Purified water                                           | 74.6    |
| Perfume                                                  | 0.2     |
|                                                          | 100.0   |

Each component was added and emulsified in the manner of Example 7. The milk lotion obtained was a stable emulsion, and action against the skin was mild.

EXAMPLE 10

Make-up cream

|                                                       | Percent |
|-------------------------------------------------------|---------|
| Spermaceti                                            | 3.0     |
| Cetyl alcohol                                         | 2.0     |
| Squalane                                              | 3.0     |
| Liquid paraffin                                       | 10.0    |
| Cholesterol                                           | 2.0     |
| Titanium oxide                                        | 5.0     |
| Iron oxide pigment                                    | 0.5     |
| Butyl para-hydroxybenzoate                            | 0.1     |
| Methyl para-hydroxybenzoate                           | 0.1     |
| Glycerol                                              | 5.0     |
| Condensation product of MC stearic acid and L-arginine | 1.0    |
| Purified water                                        | 68.1    |
| Perfume                                               | 0.2     |
|                                                       | 100.0   |

Example 7 was repeated with the exception that titanium oxide and iron oxide pigments were dispersed into oily components. The make-up cream obtained was a stable emulsion, and active against the skin was mild.

EXAMPLE 11

Water-in-oil type cream

|                                                      | Percent |
|------------------------------------------------------|---------|
| Liquid paraffin                                      | 30.0    |
| Bees wax                                             | 10.0    |
| Paraffin wax (135° F.)                               | 5.0     |
| Phytosterol                                          | 3.0     |
| Butyl para-hydroxybenzoate                           | 0.1     |
| Methyl para-hydroxybenzoate                          | 0.1     |
| Condensation product of oleic acid and L-arginine    | 2.0     |
| Purified water                                       | 49.6    |
| Perfume                                              | 0.2     |
|                                                      | 100.0   |

Each component was added and emulsified in the manner of Example 7. The water-in-oil type cream obtained was a stable emulsion, and action against the skin was mild.

EXAMPLE 12

Hydrophilic ointment

|     |                                              | Percent |
| --- | -------------------------------------------- | ------- |
| (1) | Stearyl alcohol                              | 20.0    |
| (2) | White vaseline                               | 25.0    |
| (3) | Cholesterol                                  | 2.0     |
| (4) | Propyl para-hydroxybenzoate                  | 0.2     |
| (5) | Methyl para-hydroxybenzoate                  | 0.2     |
| (6) | Propylene glycol                             | 12.0    |
| (7) | Condensation product of MC stearic acid and L-arginine | 2.0 |
| (8) | Purified water                               | 38.6    |
|     |                                              | 100.0   |

Components 1–3 were melted on a water bath in the manner of Japanese pharmacopeia (ninth revision, second section, and then stirred at a temperature of 75° C. to form a mixture.

Components 4–7 were added to component 8, i.e., purified water, and then dissolved into the purified water at a temperature of 75° C. to prepare an aqueous solution.

Thereafter, the aqueous solution as prepared above was added to the mixture, and then mixed with stirring until solidifying. The hydrophilic ointment obtained had an excellent stability, and action against the skin was mild.

EXAMPLE 13

Nutrient cream

| Squalane                                          | 20.0  |
| ------------------------------------------------- | ----- |
| Phytostanol                                       | 2.0   |
| Butyl para-hydroxybenzoate                        | 0.1   |
| Methyl para-hydroxybenzoate                       | 0.1   |
| Condensation product of isostearic acid and L-lysine | 4.0 |
| Glycerol                                          | 5.0   |
| Purified water                                    | 68.6  |
| Perfume                                           | 0.2   |
|                                                   | 100.0 |

Each component was added and emulsified in the manner of Example 7. The nutrient cream obtained was a stable emulsion, and action against the skin was mild.

EXAMPLE 14

|     |                  | Percent |
| --- | ---------------- | ------- |
| (1) | Liquid paraffin  | 20.0    |
| (2) | Cholesterol      | 2.0     |
| (3) | MC stearic acid  | 3.0     |
| (4) | L-lysine         | 1.0     |
| (5) | Purified water   | 74.0    |
|     |                  | 100.0   |

(I) Components 1–3 as described above were melted at a temperature of 80° C. to form a mixture.

(II) Component 4 as described above was added to component 5, i.e., purified water, and then dissolved into the purified water at a temperature of 80° C. to prepare an aqueous solution.

(III) Thereafter, the aqueous solution as prepared in (II) was added to the mixture as prepared in (I), and then, the resultant mixture was stirred at a temperature of 80° C. for 5 minutes to allow it to emulsify uniformly, and thereafter it was cooled while stirring.

The obtained emulsion was of a thermal resistance similar to that of the emulsion in Example I, and the emulsion was not irritating to the skin.

EXAMPLE 15

Oil-in-water type cream

|                         | Percent |
| ----------------------- | ------- |
| Glycerol tri-isooctanate | 30.0   |
| Stigmasterol            | 1.0     |
| Ergosterol              | 1.0     |
| Palmitic acid           | 2.0     |
| Myristic acid           | 3.0     |
| L-histidine             | 1.5     |
| Purified water          | 61.5    |
|                         | 100.0   |

Components as described above were treated in substantially same way as Example 14. The obtained emulsion was of sufficient stability, and o/w type cream of this emulsion was mild against the skin.

EXAMPLE 16

|     |                                               | Percent |
| --- | --------------------------------------------- | ------- |
| (1) | Liquid paraffin                               | 20.0    |
| (2) | Stearic acid monoglyceride                    | 2.0     |
| (3) | Condensation product of MC stearic acid and L-arginine | 4.0 |
| (4) | Purified water                                | 74.0    |
|     |                                               | 100.0   |

Components 1 and 2 as described above were charged into a beaker, and then melted at a temperature of 80° C. to form a mixture.

Component 3 as described above was added to the purified water contained in another beaker, and then dissolved in the purified water at a temperature of 80° C. to prepare an aqueous solution.

Thereafter, the aqueous solution as prepared above was added to the mixture. The formulation was stirred for minutes at a temperature of 80° C. to allow it to emulsify uniformly, and then cooled with stirring. A portion of the emulsion obtained was placed into a thermo-hygrostat at a temperature of 40° so as to determine a thermal resistance of the emulsion. No break of the emulsion occurred upon the lapse of 30 days. It is apparent that the emulsion obtained in Example 14 has an excellent stability.

EXAMPLES 17–21

Example 16 was repeated with the exception that isopropyl myristate, cetostearyl 2-ethylhexanoate, squalane, saturated fatty acid ($C_8$–$C_{12}$) triglyceride or castor oil was used instead of the liquid paraffin used in Example 16 as oily material. The emulsions obtained in Examples 17–21 were emulsified sufficiently like in the case of the emulsion of Example 16, and had a sufficient stability.

EXAMPLE 22

Vanishing cream

|     |                  | Percent |
| --- | ---------------- | ------- |
| (1) | MC stearic acid  | 3.0     |

-continued

|     |     | Percent |
| --- | --- | --- |
| (2) | Paraffin wax (135° F.) | 2.0 |
| (3) | Spermaceti | 5.0 |
| (4) | Cetyl alcohol | 2.0 |
| (5) | Cetyl isooctanate | 5.0 |
| (6) | Isopropyl myristate | 2.0 |
| (7) | Stearic acid monoglyceride | 3.0 |
| (8) | Butyl para-hydroxybenzoate | 0.1 |
| (9) | Methyl para-hydroxybenzoate | 0.1 |
| (10) | Condensation product of MC stearic acid and L-arginine | 2.0 |
| (11) | Glycerol | 5.0 |
| (12) | Purified water | 70.6 |
| (13) | Perfume | 0.2 |
|     |     | 100.0 |

Components 1–8 as described above were charged into a beaker, and then melted at a temperature of 80° C. to form a mixture.

Components 9–11 as described above were added to the purified water contained in another beaker, and then dissolved into the purified water at a temperature of 80° C. to prepare an aqueous solution.

Thereafter, the aqueous solution as prepared above was added to the mixture. The formulation was stirred for 5 minutes at a temperature of 80° C. to allow it to emulsify uniformly, and then cooled with stirring. Component 13, i.e., perfume was added to the emulsion at a temperature of 45° C. The vanishing cream obtained was a stable emulsion, and action against the skin was mild.

EXAMPLE 23

Cleansing cream

|     | Percent |
| --- | --- |
| Bees wax | 3.0 |
| Paraffin wax (135° F.) | 2.0 |
| Cetyl alcohol | 2.0 |
| Isopropyl palmitate | 10.0 |
| Liquid paraffin | 30.0 |
| Sorbitan monostearate | 3.0 |
| Butyl para-hydroxybenzoate | 0.1 |
| Methyl para-hydroxybenzoate | 0.1 |
| Condensation product of MC stearic acid and L-arginine | 4.0 |
| Propylene glycol | 5.0 |
| Purified water | 40.6 |
| Perfume | 0.2 |
|     | 100.0 |

Each component was added and emulsified in the manner of Example 22. The cleansing cream obtained was a stable emulsion, and action against the skin was mild.

EXAMPLE 24

Milk lotion

|     | Percent |
| --- | --- |
| Spermaceti | 3.0 |
| Bees wax | 2.0 |
| Saturated fatty acid ($C_8$–$C_{12}$) triglyceride | 10.0 |
| Stearic acid monoglyceride | 2.0 |
| Butyl para-hydroxybenzoate | 0.1 |
| Methyl para-hydroxybenzoate | 0.1 |
| Condensation product of isostearic acid and L-lysine | 4.0 |
| Glycerol | 5.0 |

-continued

|     | Percent |
| --- | --- |
| Purified water | 73.6 |
| Perfume | 0.2 |
|     | 100.0 |

Each component was added and emulsified in the manner of Example 22. The milk lotion obtained was a stable emulsion, and action against the skin was mild.

EXAMPLE 25

Make-up cream

|     | Percent |
| --- | --- |
| Cetyl alcohol | 2.0 |
| Squalane | 5.0 |
| Saturated fatty acid ($C_8$–$C_{12}$) Triglyceride | 10.0 |
| Fatty acid ester of sucrose (DAIICHI KOGYO SEIYAKU Sugar ester S-110) | 2.0 |
| Titanium oxide | 5.0 |
| Iron oxide pigment | 0.5 |
| Butyl para-hydroxybenzoate | 0.1 |
| Methyl para-hydroxybenzoate | 0.1 |
| Glycerol | 5.0 |
| Condensation product of MC stearic acid and L-lysine | 2.0 |
| Purified water | 68.1 |
| Perfume | 0.2 |
|     | 100.0 |

Example 22 was repeated with the exception that titanium oxide and iron oxide pigments were dispersed into oily components. The make-up cream obtained was a stable emulsion, and action against the skin was mild.

EXAMPLE 26

Water-in-oil type cream

|     | Percent |
| --- | --- |
| Paraffin wax (135° F.) | 5.0 |
| Bees wax | 10.0 |
| Liquid paraffin | 30.0 |
| Sorbitan monostearate | 4.0 |
| Butyl para-hydroxybenzoate | 0.1 |
| Methyl para-hydroxybenzoate | 0.1 |
| Condensation product of oleic acid and L-arginine | 2.0 |
| Purified water | 48.6 |
| Perfume | 0.2 |
|     | 100.0 |

Each component was added and emulsified in the manner of Example 22. The water-in-oil type cream obtained was a stable emulsion, and action against the skin was mild.

EXAMPLE 27

Hydrophilic ointment

|     |     | Percent |
| --- | --- | --- |
| (1) | Stearyl alcohol | 20.0 |
| (2) | White vaseline | 25.0 |
| (3) | Fatty acid ester of sucrose (DAIICHI KOGYO SEIYAKU) Sugar ester S-L18 | 4.0 |
| (4) | Propyl para-hydroxybenzoate | 0.2 |
| (5) | Methyl para-hydroxybenzoate | 0.2 |

-continued

|     |                                              | Percent |
| --- | -------------------------------------------- | ------- |
| (6) | Propylene glycol                             | 12.0    |
| (7) | Condensation product of MC stearic acid and L-arginine | 2.0 |
| (8) | Purified water                               | 36.6    |
|     |                                              | 100.0   |

Components 1 and 2 were melted on a water bath in the manner of Japanese pharmacopeia (ninth revision, second section), and then stirred at a temperature of 75° C. to form a mixture.

Components 3–7 were added to component 8, i.e., purified water, and then dissolved into the purified water at a temperature of 75° C. to prepare an aqueous solution.

Thereafter, the aqueous solution as prepared above was added to the mixture, and then mixed with stirring until solidifying. The hydrophilic ointment obtained had an excellent stability, and action against the skin was mild.

EXAMPLE 28

|     |                              | Percent |
| --- | ---------------------------- | ------- |
| (1) | Liquid paraffin              | 20.0    |
| (2) | Stearic acid monoglyceride   | 2.0     |
| (3) | MC stearic acid              | 3.0     |
| (4) | L-arginine                   | 1.0     |
| (5) | Purified water               | 74.0    |
|     |                              | 100.0   |

(I) Components 1–3 as described above were melted at a temperature of 80° C. to form a mixture.

(II) Component 4 as described above was added to component 5, i.e., purified water, and then dissolved into the purified water at a temperature of 80° C. to prepare an aqueous solution.

(III) Thereafter, the aqueous solution as prepared in (II) was added to the mixture as prepared in (I), and then, the resultant mixture was stirred at a temperature of 80° C. for 5 minutes to allow it to emulsify uniformly, and thereafter it was cooled which stirring.

The obtained emulsion was of a thermal resistance similar to that of the emulsion in Example 16, and the emulsion was not irritating to the skin.

EXAMPLE 29

Oil-in-water cream

|                          | Percent |
| ------------------------ | ------- |
| Glycerol tri-isooctarate | 10.0    |
| Stearic acid             | 2.0     |
| Myristic acid            | 1.0     |
| Palmitic acid            | 1.0     |
| Hydroxystearic acid      | 1.0     |
| Polyglycerolmonooleate   | 1.0     |
| Sorbitanmonooleate       | 2.0     |
| L-histidine              | 1.5     |
| Purified water           | 80.5    |
|                          | 100.0   |

Components as described above were treated in substantially same way as Example 28. The obtained emulsion was of sufficient stability, and o/w type cream of this emulsion was mild against the skin.

EXAMPLE 30

|     |                                              | Percent |
| --- | -------------------------------------------- | ------- |
| (1) | Liquid paraffin                              | 20.0    |
| (2) | 1,2-Alkane ($C_{15}$–$C_{18}$) diol          | 2.0     |
| (3) | Condensation product of MC stearic acid and L-arginine | 4.0 |
| (4) | Purified water                               | 74.0    |
|     |                                              | 100.0   |

Components 1 and 2 as described above were charged into a beaker, and then melted at a temperature of 80° C. to form a mixture.

Component 3 as described above was added to the purified water contained in another beaker, and then dissolved into the purified water at a temperature of 80° C. to prepare an aqueous solution.

Thereafter, the aqueous solution as prepared above was added to the mixture. The formulation was stirred for 5 minutes at a temperature of 80° C. to allow it to emulsify uniformly, and then cool with stirring. A portion of the emulsion obtained was placed into a thermohygrostat at a temperature of 40° C. so as to determine a thermal resistance of the emulsion. No break of the emulsion occurred after the lapse of 30 days. It is apparent that the emulsion obtained in Example 30 has an excellent stability.

EXAMPLES 31–35

Example 30 was repeated with the exception that isopropyl myristate, cetostearyl 2-ethylhexanoate, squalane, saturated fatty acid ($C_8$–$C_{12}$) triglyceride or castor oil was used instead of the liquid paraffin used in Example 30 as oily material. The emulsions obtained in Examples 31–35 were emulsified sufficiently similar to the emulsion of Example 30, and had a sufficient stability.

EXAMPLE 36

Vanishing cream

|      |                                              | Percent |
| ---- | -------------------------------------------- | ------- |
| (1)  | MC stearic acid                              | 3.0     |
| (2)  | Paraffin wax (135° F.)                       | 2.0     |
| (3)  | Spermaceti                                   | 5.0     |
| (4)  | Cetyl alcohol                                | 2.0     |
| (5)  | Cetyl isooctanate                            | 5.0     |
| (6)  | Isopropyl myristate                          | 2.0     |
| (7)  | Batyl alcohol                                | 2.0     |
| (8)  | Butyl para-hydroxybenzoate                   | 0.1     |
| (9)  | Methyl para-hydroxybenzoate                  | 0.1     |
| (10) | Condensation product of MC stearic acid and L-lysine | 2.0 |
| (11) | Glycerol                                     | 5.0     |
| (12) | Purified water                               | 71.6    |
| (13) | Perfume                                      | 0.2     |
|      |                                              | 100.0   |

Components 1–8 as described above were charged into a beaker, and then melted at a temperature of 80° C. to form a mixture.

Components 9–11 as described above were added to the purified water contained in another beaker, and then dissolved into the purified water at a temperature of 80° C. to prepare an aqueous solution.

Thereafter, the aqueous solution as prepared above was added to the mixture. The formulation was stirred for 5 minutes at a temperature of 80° C. to allow it to emulsify uniformly, and then cooled with stirring. Component 13, i.e., perfume was added to the emulsion at a temperature of 45° C. The vanishing cream obtained was a stable emulsion, and action against the skin was mild.

EXAMPLE 37

Cleansing cream

|  | Percent |
| --- | --- |
| Bees wax | 3.0 |
| Paraffin wax (135° F.) | 2.0 |
| Cetyl alcohol | 2.0 |
| Isopropyl palmitate | 10.0 |
| Liquid paraffin | 30.0 |
| 1,2-Alkane ($C_{15}$–$C_{18}$) diol | 2.0 |
| Butyl para-hydroxybenzoate | 0.1 |
| Methyl para-hydroxybenzoate | 0.1 |
| Condensation product of MC stearic acid and L-arginine | 4.0 |
| Propylene glycol | 5.0 |
| Purified water | 41.6 |
| Perfume | 0.9 |
|  | 100.0 |

Each component was added and emulsified in the manner of Example 36. The cleansing cream obtained was a stable emulsion, and action against the skin was mild.

EXAMPLE 38

Milk lotion

|  | Percent |
| --- | --- |
| Spermaceti | 3.0 |
| Bees wax | 2.0 |
| Saturated fatty acid ($C_8$–$C_{12}$) Triglyceride | 10.0 |
| 1,2-Alkane ($C_{15}$–$C_{18}$) diol | 2.0 |
| Butyl para-hydroxybenzoate | 0.1 |
| Methyl para-hydroxybenzoate | 0.1 |
| Condensation product of isostearic acid and L-lysine | 4.0 |
| Glycerol | 5.0 |
| Purified water | 73.6 |
| Perfume | 0.2 |
|  | 100.0 |

Each component was added and emulsified in the manner of Example 36. The milk lotion obtained was a stable emulsion, and action against the skin was mild.

EXAMPLE 39

Make-up cream

|  | Percent |
| --- | --- |
| Cetyl alcohol | 2.0 |
| Squalane | 5.0 |
| Saturated fatty acid ($C_8$–$C_{12}$) triglyceride | 10.0 |
| 1,2-Alkane ($C_{15}$–$C_{18}$) diol | 2.0 |
| Titanium oxide | 5.0 |
| Iron oxide pigment | 0.5 |
| Butyl para-hydroxybenzoate | 0.1 |
| Methyl para-hydroxybenzoate | 0.1 |
| Glycerol | 5.0 |
| Condensation product of MC stearic acid and L—arginine | 2.0 |
| Purified water | 68.1 |
| Perfume | 0.2 |
|  | 100.0 |

Example 36 was repeated with the exception that titanium oxide and iron oxide pigments were dispersed into oily components. The make-up cream obtained was a stable emulsion, and action against the skin was mild.

EXAMPLE 40

Water-in-oil type cream

|  | Percent |
| --- | --- |
| Liquid paraffin | 30.0 |
| Bees wax | 10.0 |
| Paraffin wax (135° F.) | 5.0 |
| 1,2-Alkane ($C_{15}$–$C_{18}$) diol | 3.0 |
| Butyl para-hydroxybenzoate | 0.1 |
| Methyl para-hydroxybenzoate | 0.1 |
| Condensation product of oleic acid and L—arginine | 2.0 |
| Purified water | 49.6 |
| Perfume | 0.2 |
|  | 100.0 |

Each component was added and emulsified in the manner of Example 36. The water-in-oil type cream obtained was a stable emulsion, and action against the skin was mild.

EXAMPLE 41

Hydrophilic ointment

|  | Percent |
| --- | --- |
| (1) Stearyl alcohol | 20.0 |
| (2) White vaseline | 25.0 |
| (3) Batyl alcohol | 1.0 |
| (4) Propyl para-hydroxybenzoate | 0.2 |
| (5) Methyl para-hydroxybenzoate | 0.2 |
| (6) Propylene glycol | 12.0 |
| (7) Condensation product of isostearic acid and L—arginine | 4.0 |
| (8) Purified water | 37.6 |
|  | 100.0 |

Components 1-3 were melted on a water bath in the manner of Japanese pharmacopeia (ninth revision, second section), and then stirred at a temperature of 75° C. to form a mixture.

Components 4-7 were added to component 8, i.e., purified water, and then dissolved into the purified water at a temperature of 75° C. to prepare an aqueous solution.

Thereafter, the aqueous solution as prepared above was added to the mixture, and then mixed with stirring until solidifying. The hydrophilic ointment obtained had an excellent stability, and action against the skin was mild.

EXAMPLE 42

|  | Percent |
| --- | --- |
| (1) Liquid paraffin | 20.0 |
| (2) 1,2-Alkane ($C_{15}$–$C_{18}$) diol | 2.0 |
| (3) MC stearic acid | 3.0 |
| (4) L—arginine | 1.0 |
| (5) Purified water | 74.0 |
|  | 100.0 |

(I) Components 1-3 as described above were melted at a temperature of 80° C. to form a mixture.

(II) Component 4 as described above was added to component 5, i.e., purified water, and then dissolved into the purified water at a temperature of 80° C. to prepare an aqueous solution.

(III) Thereafter, the aqueous solution as prepared in (II) was added to the mixture as prepared in (I), and then, the resultant mixture was stirred at a temperature of 80° C. for 5 minutes to allow it to emulsify uniformly, and thereafter it was cooled while stirring.

The obtained emulsion was of a thermal resistance similar to that of the emulsion in Example 30, and the emulsion was not irritating to the skin.

EXAMPLE 43

Oil-in-water cream

|  | Percent |
|---|---|
| Glycerol tri-isooctarate | 10.0 |
| Stearic acid | 2.0 |
| Myristic acid | 1.0 |
| Palmitic acid | 1.0 |
| Hydroxystearic acid | 1.0 |
| 1,2-Alkane ($C_{15}$-$C_{18}$) diol | 1.0 |
| L—histidine | 1.5 |
| Purified water | 81.5 |
|  | 100.0 |

Components as described above were treated in substantially same way as Example 42. The obtained emulsion was of sufficient stability, and o/w type cream of this emulsion was mild against the skin.

EXAMPLE 44

|  | Percent |
|---|---|
| (1) Liquid paraffin | 20.0 |
| (2) Lecithin | 4.0 |
| (3) Condensation product of hydroxystearic acid and L—lysine | 4.0 |
| (4) Purified water | 72.0 |
|  | 100.0 |

Components 1 and 2 as described above were charged into a beaker, and then melted at a temperature of 80° C. to form a mixture.

Component 3 as described above was added to the purified water contained in another beaker, and then dissolved into the purified water at a temperature of 80° C. to prepare an aqueous solution.

Thereafter, the aqueous solution as prepared above was added to the mixture. The formulation was stirred for 5 minutes at a temperature of 80° C. to allow it to emulsify uniformly, and then cooled with stirring. A portion of the emulsion obtained was placed into a thermo-hygrostat at a temperature of 40° C. so as to determine a thermal resistance of the emulsion. No break of the emulsion occurred after the lapse of 30 days. It is apparent that the emulsion obtained in Example 44 has an excellent stability.

EXAMPLES 45-49

Example 44 was repeated with the exception that isopropyl myristate, cetostearyl 2-ethylhexanoate, squalane, saturated fatty acid ($C_8$-$C_{12}$) triglyceride or caster oil was used instead of the liquid paraffin used in Example 44 as oily material. The emulsions obtained in Examples 45-49 were emulsified sufficiently like in the case of the emulsion of Example 44, and had a sufficient stability.

EXAMPLE 50

Vanishing cream

|  | Percent |
|---|---|
| (1) MC stearic acid | 3.0 |
| (2) Paraffin wax (135° F.) | 2.0 |
| (3) Spermaceti | 5.0 |
| (4) Cetyl alcohol | 2.0 |
| (5) Cetyl isooctanate | 5.0 |
| (6) Isopropyl myristate | 2.0 |
| (7) Lecithin | 1.0 |
| (8) Butyl para-hydroxybenzoate | 0.1 |
| (9) Methyl para-hydroxybenzoate | 0.1 |
| (10) Condensation product of MC stearic acid and L—arginine | 2.0 |
| (11) Glycerol | 5.0 |
| (12) Purified water | 72.6 |
| (13) Perfume | 0.2 |
|  | 100.0 |

Components 1-8 as described above were charged into a beaker, and then melted at a temperature of 80° C. to form a mixture.

Components 9-11 as described above were added to the purified water contained in another beaker, and then dissolved into the purified water at a temperature of 80° C. to prepare an aqueous solution.

Thereafter, the aqueous solution as prepared above was added to the mixture. The formulation was stirred for 5 minutes at a temperature of 80° C. to allow it to emulsify uniformly and then cooled with stirring. Component 13, i.e., perfume was added to the emulsion at a temperature of 45° C. The vanishing cream obtained was a stable emulsion, and action against the skin was mild.

EXAMPLE 51

Cleansing cream

|  | Percent |
|---|---|
| Bees wax | 3.0 |
| Paraffin wax (135° F.) | 2.0 |
| Cetyl alcohol | 2.0 |
| Isopropyl palmitate | 10.0 |
| Liquid paraffin | 30.0 |
| Lecithin | 1.0 |
| Butyl para-hydroxybenzoate | 0.1 |
| Methyl para-hydroxybenzoate | 0.1 |
| Condensation product of MC stearic acid and L—arginine | 4.0 |
| Propylene glycol | 5.0 |
| Purified water | 42.6 |
| Perfume | 0.2 |
|  | 100.0 |

Each component was added and emulsified in the manner of Example 50. The cleansing cream obtained was a stable emulsion, and action against the skin was mild.

EXAMPLE 52

Milk lotion

|  | Percent |
|---|---|
| Spermaceti | 3.0 |
| Cetyl alcohol | 2.0 |
| Bees wax | 2.0 |
| Saturated fatty acid ($C_8$-$C_{12}$) triglyceride | 10.0 |

-continued

| | Percent |
|---|---|
| Lecithin | 2.0 |
| Butyl para-hydroxybenzoate | 0.1 |
| Methyl para-hydroxybenzoate | 0.1 |
| Condensation product of isostearic acid and L—lysine | 4.0 |
| Glycerol | 5.0 |
| Purified water | 71.6 |
| Perfume | 0.2 |
| | 100.0 |

Each component was added and emulsified in the manner of Example 50. The milk lotion obtained was a stable emulsion, and action against the skin as mild.

EXAMPLE 53

Make-up cream

| | Percent |
|---|---|
| Cetyl alcohol | 2.0 |
| Squalane | 5.0 |
| Saturated fatty acid ($C_8$-$C_{12}$) triglyceride | 10.0 |
| Lecithin | 3.0 |
| Titanium oxide | 5.0 |
| Iron oxide pigment | 0.5 |
| Butyl para-hydroxybenzoate | 0.1 |
| Methyl para-hydroxybenzoate | 0.1 |
| Glycerol | 5.0 |
| Condensation product of MC stearic acid and L—arginine | 2.0 |
| Purified water | 67.1 |
| Perfume | 0.2 |
| | 100.0 |

Example 50 was repeated with the exception that titanium oxide and iron oxide pigments were dispersed into oily components. The make-up cream obtained was a stable emulsion, and action against the skin was mild.

EXAMPLE 54

Hydrophilic ointment

| | | Percent |
|---|---|---|
| (1) | Stearyl alcohol | 20.0 |
| (2) | White vaseline | 25.0 |
| (3) | Lecithin | 1.0 |
| (4) | Propyl para-hydroxybenzoate | 0.2 |
| (5) | Methyl para-hydroxybenzoate | 0.2 |
| (6) | Propylene glycol | 12.0 |
| (7) | Condensation product of stearic acid and L—arginine | 4.0 |
| (8) | Purified water | 37.6 |
| | | 100.0 |

Components 1 and 2 were melted on a water bath in the manner of Japanese Pharmacopeia (ninth revision, second section), and then stirred at a temperature of 75° C. to form a mixture.

Components 3–7 were added to component 8, i.e., purified water, and then dissolved into the purified water at a temperature of 75° C. to prepare an aqueous solution.

Thereafter, the aqueous solution as prepared above was added to the mixture, and then mixed with stirring until solidifying. The hydrophilic ointment obtained had an excellent stability, and action against the skin was mild.

EXAMPLE 55

| | | Percent |
|---|---|---|
| (1) | Liquid paraffin | 20.0 |
| (2) | Lecithin | 4.0 |
| (3) | Hydroxystearic acid | 3.0 |
| (4) | L—lysine | 1.0 |
| (5) | Purified water | 72.0 |
| | | 100.0 |

(I) Components 1–3 as described above were melted at a temperature of 80° C. to form a mixture.

(II) Component 4 as described above was added to component 5, i.e., purified water, and then dissolved into the purified water at a temperature of 80° C. to prepare an aqueous solution.

(III) Thereafter, the aqueous solution as prepared in (II) was added to the mixture as prepared in (I), and then, the resultant mixture was stirred at a temperature of 80° C. for 5 minutes to allow it to emulsify uniformly, and thereafter it was cooled while stirring.

The obtained emulsion was of a thermal resistance similar to that of the emulsion in Example 44, and the emulsion was not irritating to the skin.

EXAMPLE 56

Water-in-oil type cream

| | Percent |
|---|---|
| Glycerol tri-isooctarate | 30.0 |
| Stearic acid | 3.0 |
| Myristic acid | 1.0 |
| Palmitic acid | 1.0 |
| Bees wax | 5.0 |
| Yolk lecithin | 3.0 |
| L—histidine | 1.5 |
| Purified water | 55.5 |
| | 100.0 |

Components as described above were treated in substantially same way as Example 55. The obtained emulsion was of sufficient stability, and w/o type cream of this emulsion was mild against the skin.

EXAMPLE 57

| | | Percent |
|---|---|---|
| (1) | Liquid paraffin | 20.0 |
| (2) | Stearyl alcohol | 2.0 |
| (3) | Condensation product of myristic acid and L—arginine | 2.0 |
| (4) | Purified water | 76.0 |
| | | 100.0 |

Components 1 and 2 as described above were charged into a beaker, and then melted at a temperature of 80° C. to form a mixture.

Component 3 as described above was added to the purified water contained in another beaker, and then dissolved into the purified water at a temperature of 80° C. to prepare an aqueous solution.

Thereafter, the aqueous solution as prepared above was added to the mixture. The formulation was stirred for 5 minutes at a temperature of 80° C. to allow it to emulsify uniformly, and then cooled with stirring. A portion of the emulsion obtained was placed into a thermo-hygrostat at a temperature of 40° C. so as to determine a thermal resistance of the emulsion. No break of the emulsion after the lapse of 30 days. It is apparent that the emulsion obtained in Example 57 has an excellent stability.

EXAMPLES 58–62

Example 57 was repeated with the exception that isopropyl myristate, cetostearyl 2-ethylhexanoate, squalane, saturated fatty acid ($C_8$–$C_{12}$) triglyceride or castor oil was used instead of the liquid paraffin used in Example 57 as oily material. The emulsions obtained in Examples 58–62 were emulsified sufficiently like in the case of the emulsion of Example 57, and had a sufficient stability.

EXAMPLE 63

Vanishing cream

|  | Percent |
|---|---|
| (1) MC stearic acid | 5.0 |
| (2) Paraffin wax (135° F.) | 2.0 |
| (3) Spermaceti | 5.0 |
| (4) Stearyl alcohol | 3.0 |
| (5) Cetyl isooctanate | 5.0 |
| (6) Isopropyl mysistate | 2.0 |
| (7) Butyl para-hydroxybenzoate | 0.1 |
| (8) Methyl para-hydroxybenzoate | 0.1 |
| (9) Condensation product of stearic acid and L—lysine | 2.0 |
| (10) Glycerol | 5.0 |
| (11) Purified water | 70.6 |
| (12) Perfume | 0.2 |
|  | 100.0 |

Components 1–7 as described above were charged into a beaker, and then melted at a temperature of 80° C. to form a mixture.

Components 8–10 as described above were added to the purified water contained in another beaker, and then dissolved into the purified water at a temperature of 80° C. to prepare an aqueous solution.

Thereafter, the aqueous solution as prepared above was added to the mixture. The formulation was stirred for 5 minutes at a temperature of 80° C. to allow it to emulsify uniformly, and then cooled with stirring. Component 12, i.e., perfume was added to the emulsion at a temperature of 45° C. The vanishing cream obtained was a stable emulsion, and action against the skin was mild.

EXAMPLE 64

Cleansing cream

|  | Percent |
|---|---|
| Bees wax | 3.0 |
| Paraffin wax (135° F.) | 2.0 |
| Isopropyl palmitate | 10.0 |
| Liquid paraffin | 30.0 |
| Behenyl alcohol | 3.0 |
| Butyl para-hydroxybenzoate | 0.1 |
| Methyl para-hydroxybenzoate | 0.1 |
| Condensation product of palmitic acid and L—arginine | 3.0 |
| Maltitol (50% aqueous solution) | 5.0 |
| Purified water | 43.6 |
| Perfume | 0.2 |
|  | 100.0 |

Each component was added and emulsified in the manner of Example 63. The cleansing cream obtained was a stable emulsion, and action against the skin was mild.

EXAMPLE 65

Milk lotion

|  | Percent |
|---|---|
| Spermaceti | 3.0 |
| Bees wax | 2.0 |
| Squalane | 5.0 |
| Isopropyl myristate | 5.0 |
| Oleyl alcohol | 2.0 |
| Butyl para-hydroxybenzoate | 0.1 |
| Methyl para-hydroxybenzoate | 0.1 |
| Condensation product of MC stearic acid and L—arginine | 2.0 |
| Glycerol | 5.0 |
| Purified water | 75.6 |
| Perfume | 0.2 |
|  | 100.0 |

Each component was added and emulsified in the manner of Example 63. The milk lotion obtained was a stable emulsion, and action against the skin was mild.

EXAMPLE 66

Make-up cream

|  | Percent |
|---|---|
| Squalane | 5.0 |
| Liquid paraffin | 10.0 |
| Cetostearyl alcohol | 3.0 |
| Butyl para-hydroxybenzoate | 0.1 |
| Methyl para-hydroxybenzoate | 0.1 |
| Condensation product of stearic acid and L—arginine | 1.5 |
| Propylene glycol | 5.0 |
| Titanium oxide | 5.0 |
| Iron oxide pigment | 0.5 |
| Purified water | 69.6 |
| Perfume | 0.2 |
|  | 100.0 |

Example 63 was repeated with the exception that titanium oxide and iron oxide pigments were dispersed into oily components. The make-up cream obtained was a stable emulsion, and action against the skin was mild.

EXAMPLE 67

Water-in-oil type cream

|  | Percent |
|---|---|
| Liquid paraffin | 25.0 |
| Bees wax | 10.0 |
| Paraffin wax (135° F.) | 5.0 |
| Cetyl alcohol | 3.0 |
| Butyl para-hydroxybenzoate | 0.1 |
| Methyl para-hydroxybenzoate | 0.1 |
| Condensation product of isostearic acid and L—arginine | 2.0 |
| Purified water | 54.6 |
| Perfume | 0.2 |
|  | 100.0 |

Each component was added and emulsified in the manner of Example 63. The water-in-oil type cream obtained was a stable emulsion, and action against the skin was mild.

EXAMPLE 68

Germicidal cream

| | Percent |
|---|---|
| White vaseline | 5.0 |
| Liquid paraffin | 5.0 |
| Isopropyl myristate | 5.0 |
| Cetyl alcohol | 5.0 |
| Butyl para-hydroxybenzoate | 0.1 |
| Methyl para-hydroxybenzoate | 0.1 |
| Condensation product of stearic acid and L—lysine | 2.0 |
| Gluconic acid chlorhexizine (20 w/v %) | 5.0 |
| Maltitol (50 w/w %) | 5.0 |
| Purified water | 67.8 |
| | 100.0 |

Each component was added and emulsified in the manner of Example 63. The germicidal cream obtained was a stable emulsion, and action against the skin was mild.

EXAMPLE 69

Hydrophilic ointment

| | Percent |
|---|---|
| (1) Stearyl alcohol | 20.0 |
| (2) White vaseline | 25.0 |
| (3) Propyl para-hydroxybenzoate | 0.2 |
| (4) Methyl para-hydroxybenzoate | 0.2 |
| (5) Propylene glycol | 12.0 |
| (6) Condensation product of MC stearic acid and L—lysine | 3.0 |
| (7) Purified water | 39.6 |
| | 100.0 |

Components 1 and 2 were melted on a water bath in the manner of Japanese Pharmacopeia (ninth revision, second section), and then stirred at a temperature of 75° C. to form a mixture.

Compounds 3–6 were added to component 7, i.e., the purified water, and then dissolved into the purified water at a temperature of 75° C. to prepare an aqueous solution.

Thereafter, the aqueous solution as prepared above was added to the mixture, and then mixed with stirring until solidifying. The hydrophilic ointment obtained had an excellent stability, and action against the skin was mild.

EXAMPLE 70

| | Percent |
|---|---|
| (1) Liquid paraffin | 20.0 |
| (2) Stearyl alcohol | 2.0 |
| (3) Myristic acid | 1.5 |
| (4) L—arginine | 0.5 |
| (5) Purified water | 76.0 |
| | 100.0 |

(I) Components 1–3 as described above were melted at a temperature of 80° C. to form a mixture.

(II) Component 4 as described above was added to component 5, i.e., purified water, and then dissolved into the purified water at a temperature of 80° C. to prepare an aqueous solution.

(III) Thereafter, the aqueous solution as prepared in (II) was added to the mixture as prepared in (I), and then, the resultant mixture was stirred at a temperature of 80° C. for 5 minutes to allow it to emulsify uniformly, and thereafter it was cooled while stirring.

The obtained emulsion was of a thermal resistance similar to that of the emulsion in Example 57, and the emulsion was not irritating to the skin.

EXAMPLE 71

Cream

| | Percent |
|---|---|
| Glycerol tri-isooctarate | 30.0 |
| Octadecanol glycol | 1.0 |
| Iso-cetylalcohol | 1.0 |
| Behenic acid | 3.0 |
| Oleic acid | 1.0 |
| L—histidine | 1.0 |
| L—arginine | 0.3 |
| Purified water | 62.7 |
| | 100.0 |

Components as described above were treated as substantially same way as Example 70. The obtained emulsion was of sufficient stability, and o/w type cream of this emulsion was mild against the skin.

Although the present invention has been described by preferred embodiments, it is to be understood that variations and modifications may be resorted to as will be apparent to those skilled in the art. Such variations and modifications are to be considered within the purview and scope of the claims appended hereto.

What is claimed is:

1. A stable emulsifier composition which comprises an interfacial complex comprising the reaction product of (a) a condensation product of a fatty acid selected from the group consisting of stearic acid, oleic acid, and myristic acid, and a basic amino-acid selected from the group consisting of arginine, lysine, $\beta$-lysine, and hydroxylsine, and (b) a secondary compound selected from the group consisting of a sterol compound, a fatty acid ester of a polyhydric alcohol, a diol compound having hydroxyl groups at the $\alpha$ and $\beta$ positions, a glycerophosphoric acid ester, a higher alcohol and mixtures thereof, said condensation products and said secondary compound being at a weight ratio ranging from 20:1 to 1:20, and said composition being non-irritating to the skin.

2. The emulsifier composition according to claim 1, wherein the sterol compound is selected from the group consisting of cholesterol, cholestanol, phytosterols, phytostanol obtained by hydrogenation of phytosterol, ergosterol, brassicasterol, spinasterol, fucosterol, and sterol mixtures contained in unsaponifiable matter of lanolin, and mixtures thereof.

3. The emulsifier composition according to claim 2, wherein the glycerophosphoric acid ester is a compound having the following formula

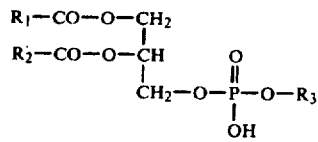

wherein $R_1$ and $R_2$ are hydrogen, saturated hydrocarbon having 8 to 40 carbon atoms or unsaturated hydrocarbon having 8 to 40 carbon atoms respectively, and R$_3$ is hydrogen, choline, ethanolamine, serine, inositol, glycerol, N-methylethanolamine or N,N-dimethylethanolamine.

4. The emulsifier composition according to claim 3 wherein the glycerophosphoric acid ester is selected from the group consisting of phosphatidic acid, phosphatidyl choline, phosphatidyl ethanolamine, phosphatidyl serine, phosphatidyl-N-methylethanolamine, phosphatidyl-N,N-dimethylethanolamine, phosphatidyl glycerol, phosphatidyl inositol, lysophosphatidyl choline, and mixtures thereof.

5. The emulsifier composition according to claim 2, wherein the higher alcohol is selected from the group consisting of straight chain saturated higher alcohols having 8 to 40 carbon atoms, branched chain saturated higher alcohols having 8 to 40 carbon atoms, straight chain unsaturated higher alcohols having 8 to 40 carbon atoms, branched chain unsaturated higher alcohols having 8 to 40 carbon atoms, and mixtures thereof.

6. The emulsifier composition according to claim 5 wherein the higher alcohol is selected from the group consisting of lauryl alcohol, myristyl alcohol, cetyl alcohol, stearyl alcohol, behenyl alcohol, beef tallow alcohol, sperm alcohol, oleyl alcohol, cetostearyl alcohol, isostearyl alcohol, 2-octyldodecanol, 2-hexyldecanol, octyl alcohol, decyl alcohol, arachidic alcohol, coconut alcohol, lanolin alcohol, isocetyl alcohol, octadecenol glycol, and mixtures thereof.

7. The emulsifier composition according to claim 2, where the polyhydric alcohol used for production of the fatty acid ester of polyhydric alcohol is selected from the group consisting of glycerol, tetraglycerol, pentaglycerol, hexaglycerol, decaglycerol, pentaerythritol, sorbitan, sorbitol, mannitol, sucrose and mixtures thereof.

8. The composition of claim 7 where the fatty acid used for production of the fatty acid ester of polyhydric alcohol is selected from the group consisting of straight-chain saturated fatty acids, branched chain saturated fatty acids, straight chain unsaturated fatty acids, branched chain unsaturated fatty acids, and mixtures thereof.

9. The composition of claim 8 where the fatty acid used for production of the fatty acid ester of polyhydric alcohol is selected from the group consisting of caprylic acid, capric acid, lauric acid, myristic acid, palmitic acid, stearic acid, behenic acid, oleic acid, linoleic acid, linolenic acid, ricinoleic acid, isostearic acid, undecylenic acid, hydroxystearic acid, cerotic acid, abietic acid, isooctanoic acid, isohexadecanoic acid, 2-ethylhexadecanoic acid, lanolin fatty acid, 12-methyl-9,11-octadecadienoic acid and mixtures thereof.

10. The composition according to claim 2 wherein the diol compound having groups at $\alpha$ and $\beta$ positions is selected from the group consisting of 1,2-long chain alkane diols having 10 to 40 carbon atoms, glycerol monoalkyl ethers having 8 to 40 carbon atoms, and mixtures thereof.

11. The composition according to claim 10 where the 1,2-long chain alkane diols are selected from the group consisting of reaction products obtained by hydroxylation of $\alpha$-olefinic compounds, straight chain iso-1,2-long chain alkane diols present in unsaponifiable matters of natural lanolin, straight chain antiiso-1,2-long chain alkane diols present in unsaponifiable matters of natural lanolin, and mixtures thereof.

12. The composition according to claim 10 where the glycerol monoalkyl ethers are selected from the group consisting of glycerol monomyristyl ether obtained by reacting glycerol monosodium with myristyl sulfate, glycerol monolauryl ether obtained by reacting glycerol monosodium with lauryl sulfate, chimyl alcohol C$_{16}$H$_{33}$OCH$_2$CH(OH)CH$_2$OH, batyl alcohol C$_{18}$H$_{37}$OCH$_2$CH(OH)CH$_2$OH, celakyl alcohol C$_{18}$H$_{35}$OCH$_2$CH(OH)CH$_2$OH, and mixtures thereof.

13. A method of preparing a stable emulsifier composition which comprises reacting a fatty acid selected from the group consisting of stearic acid, oleic acid and myristic acid, and a basic amino-acid selected from the group consisting of arginine, lysine, $\beta$-lysine, and hydroxylysine, to form a condensation product, and reacting the condensation product with a secondary compound selected from the group consisting of a sterol compound, a fatty acid ester of a polyhydric alcohol, a diol compound having hydroxyl groups at the $\alpha$ and $\beta$ positions, a glycerophosphoric acid ester, a higher alcohol and mixtures thereof, said condensation product and said secondary compound being at a weight ratio ranging from 20:1 to 1:20, to form an interfacial complex, said emulsifier composition being non-irritating to the skin.

* * * * *